United States Patent
Huang

[11] Patent Number: 5,891,098
[45] Date of Patent: Apr. 6, 1999

[54] SAFETY INTRAVENOUS CATHETER

[76] Inventor: Robert Huang, 2F, No. 2, Alley 1, Lane 177, Ching-Hsing Road, Taipei, Taiwan

[21] Appl. No.: 134,933

[22] Filed: Aug. 17, 1998

[51] Int. Cl.[6] .................................................. A61M 5/178
[52] U.S. Cl. ......................... 604/164; 604/198; 604/263; 128/919
[58] Field of Search .................. 604/158, 160, 604/161, 162, 163, 165, 171, 181, 192, 197, 198, 263; 128/919

[56] References Cited

U.S. PATENT DOCUMENTS

| | | | |
|---|---|---|---|
| 5,120,320 | 6/1992 | Fayngold | 604/177 |
| 5,279,590 | 1/1994 | Sinko et al. | 604/263 |
| 5,520,654 | 5/1996 | Wahlberg | 604/164 |
| 5,651,772 | 7/1997 | Arnett | 604/164 |
| 5,797,882 | 8/1998 | Purdy et al. | 604/164 |

*Primary Examiner*—Wynn Wood Coggins
*Assistant Examiner*—LoAn H. Thanh
*Attorney, Agent, or Firm*—Rosenberg, Klein & Bilker

[57] ABSTRACT

A safety intravenous catheter including a housing, a metal needle, a plastic needle and a sheath. The metal needle is slidably fitted in the housing. The metal needle can be extended out of the housing or entirely retracted into the housing. In both the extended and retracted positions, the metal needle can be locked by means of pressing and pulling a depression block of an upper resilient plate formed on top face of the metal needle. A projecting block of a lower resilient plate of the metal needle is engaged in an engaging aperture of the housing, whereby the metal needle is prevented from extending out of the housing so as to ensure safety of medical personnel.

3 Claims, 3 Drawing Sheets

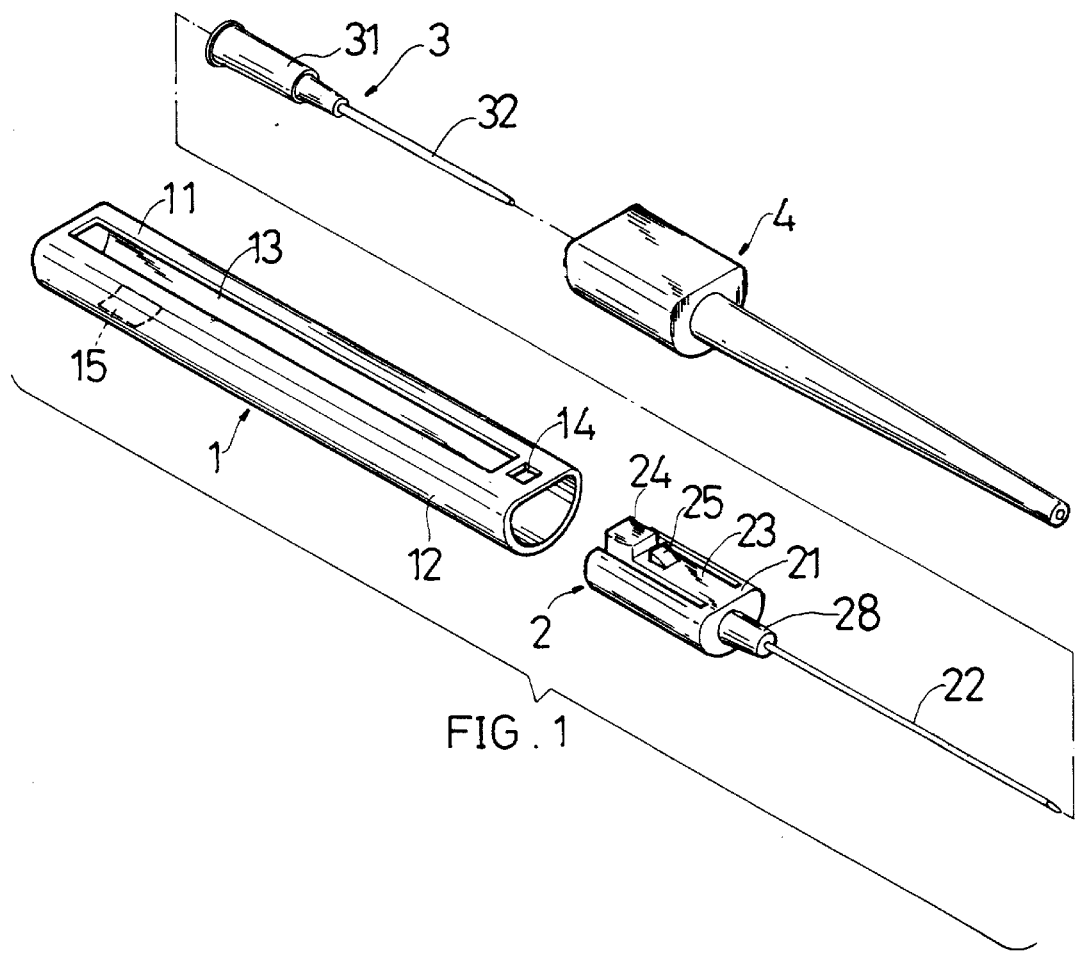
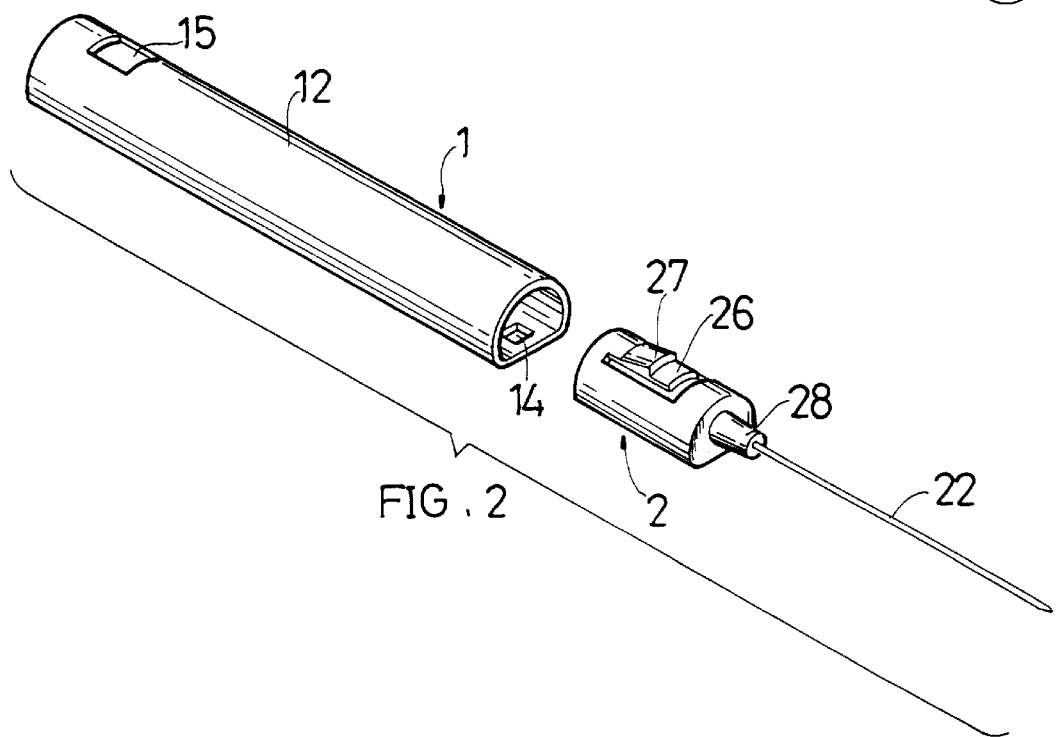

5,891,098

SAFETY INTRAVENOUS CATHETER

BACKGROUND OF THE INVENTION

The present invention relates to a safety intravenous catheter, and more particularly to an intravenous catheter which is able to avoid impalement of medical personnel or cleaner by the metal needle.

FIG. 6 shows an existing intravenous catheter in which a flexible plastic needle 82 fitted around a metal needle 81. After the metal needle 81 together with the plastic needle 82 is inserted into the vein, the metal needle 81 is extracted and then the plastic needle 82 is connected with a catheter for infusion of liquid medicine. However, after the metal needle 81 is extracted, a sheath 83 must be fitted onto the metal needle 81 so as to avoid contamination or impalement of other people, which will lead to affection with B type hepatitis, Acquired Immunodeficiency Syndrome (briefly called as AIDS), etc. After the metal needle 81 is extracted out, the metal needle 81 must be immediately fitted into the sheath 83. Otherwise, the blood in the vein will quickly flow out from the plastic needle 82. Under such emergent circumstance, it often takes place that the metal needle 81 impales the finger of the medical personnel to threaten the life of the medical personnel.

In addition, it often takes place that the sheath 83 is detached from the metal needle 81 due to collision and compression during transporting. This will expose the metal needle 81 which is seriously dangerous to the cleaner for transporting the medical waste.

SUMMARY OF THE INVENTION

It is therefore a primary object of the present invention to provide a safety intravenous catheter. By means of pressing and pulling a depression block of an upper resilient plate formed on top face of the metal needle, the metal needle can be entirely retracted into the housing. A projecting block of a lower resilient plate of the metal needle is engaged in an engaging aperture of the housing, whereby the metal needle is prevented from extending out of the housing so as to ensure safety of medical personnel.

It is a further object of the present invention to provide a safety intravenous catheter which is able to avoid impalement of medical personnel and cleaner as well as transporting worker by medical waste and ensure safety of these persons.

According to the above objects, the safety intravenous catheter of the present invention includes:

a housing having a semicircular cross-section and a top face and a bottom face, the top face being formed with a slide slot axially extending along the housing and penetrating into the interior of the housing, the housing being formed with a through hole between one end thereof and the slide slot, this end being an open end, while the other end of the housing being a close end, the bottom face being formed with an engaging aperture near the close end of the housing;

a metal needle having a fitting section fitted into the housing, one end of the fitting section being connected with a metal-made hard needle protruding out of the housing, a substantially conic connecting section being connected between the hard needle and the fitting section, a top face of the fitting section having an upper resilient plate one end of which is connected with the fitting section, the upper resilient plate having a depression block slidable within the slide slot and upward projecting from the slide slot, one side of the depression block having a protuberance for fitting into the through hole, a bottom face of the fitting section having a lower resilient plate, one end of the lower resilient plate being connected with the fitting section, the lower resilient plate having a projecting block for fitting into the engaging aperture;

a plastic needle having a needle holder for fitting with the connecting section of the metal needle, one end of the needle holder having a plastic-made soft needle for fitting around the hard needle, the soft needle having a length slightly shorter than that of the hard needle; and a sheath fitting around the metal needle for preventing the hard needle thereof from being exposed. The present invention can be best understood through the following description and accompanying drawings, wherein:

BRIEF DESCRIPTION OF THE DRAWINGS

FIG. 1 is a perspective exploded view of the present invention;

FIG. 2 is a perspective exploded view of the present invention seen in another direction;

DETAILED DESCRIPTION OF THE PREFERRED EMBODIMENT

Figure 3:
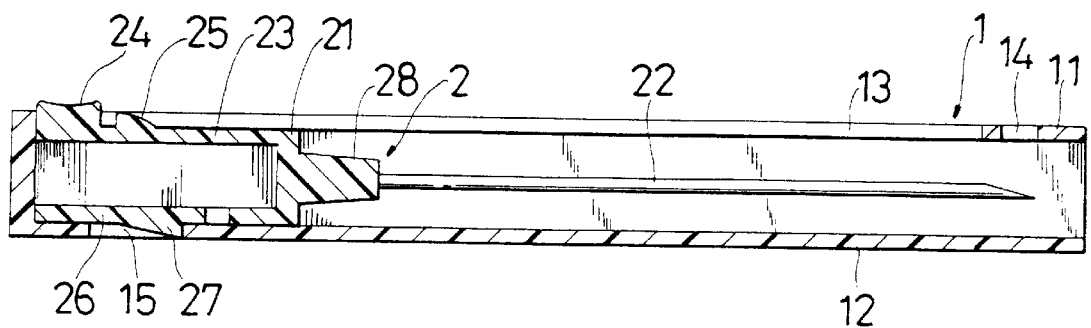
FIG. 3 is a sectional view of the present invention in which the metal needle is retracted into the housing.

Please refer to FIGS. 1 to 5. The present invention includes:

a housing 1 having a semicircular cross-section and a plane section 11 on top face and an arch section 12 on bottom face, the plane section 11 being formed with a slide slot 13 axially extending along the housing 1 and penetrating into the interior of the housing 1, the housing 1 being formed with a through hole 14 between one end thereof and the slide slot 13, this end being an open end, while the other end of the housing 1 being a close end, the arch section 12 being formed with an engaging aperture 15 near the close end of the housing 1;

a metal needle 2 having a fitting section 21 fitted into the housing 1, the fitting section 21 being a casing having a semicircular cross-section, one end of the fitting section 21 being connected with a metal-made hard needle 22 protruding out of the housing 1, a substantially conic connecting section 28 being connected between the hard needle 22 and the fitting section 21, a top face of the fitting section 21 having an upper resilient plate 23 one end of which is connected with the fitting section 21, two sides of the upper resilient plate 23 being separated from the fitting section 21, the upper resilient plate 23 having a depression block 24 slidable within the slide slot 13 and upward projecting from the slide slot 13, one side of the depression block 24 having a protuberance 25 for fitting into the through hole 14 and preventing the metal needle 2 from being retracted into the housing 1, a bottom face of the-fitting section 21 having a lower resilient plate 26, one end of the lower resilient plate 26 being connected with the fitting section 21, the lower resilient plate 26 having a projecting block 27 for fitting into the engaging aperture 15, the projecting block 27 having a height substantially equal to the depth of the engaging aperture 15;

a plastic needle 3 having a needle holder 31 for fitting with the connecting section 28 of the metal needle 2, one end of the needle holder 31 having a plastic-made soft needle 32 for fitting around the hard needle 22, the soft needle 32 having a length slightly shorter than that of the hard needle 22; and a sheath 4 fitting around the metal needle 2 for preventing the hard needle 22 thereof from being exposed.

Figure 4:
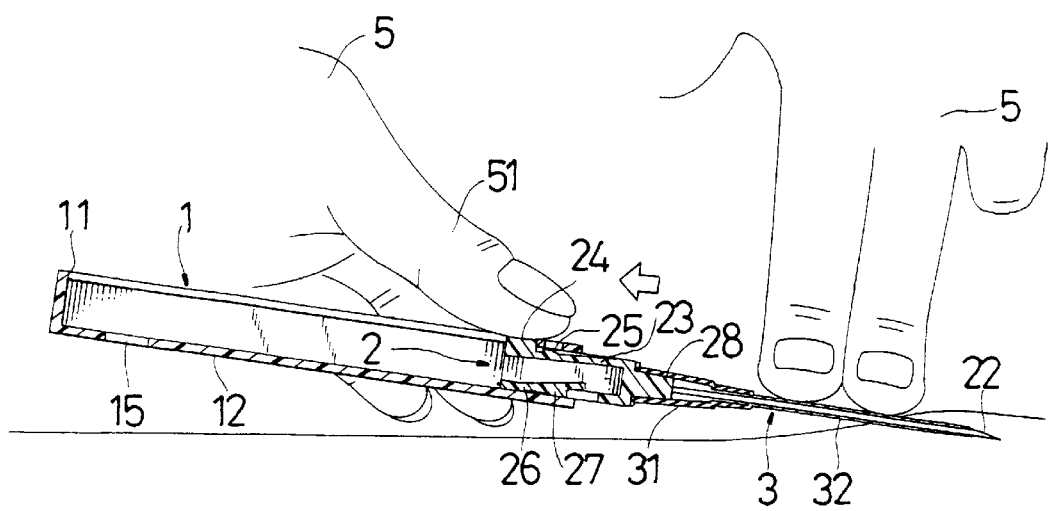
FIG. 4 shows the use of the present invention.
Figure 5:
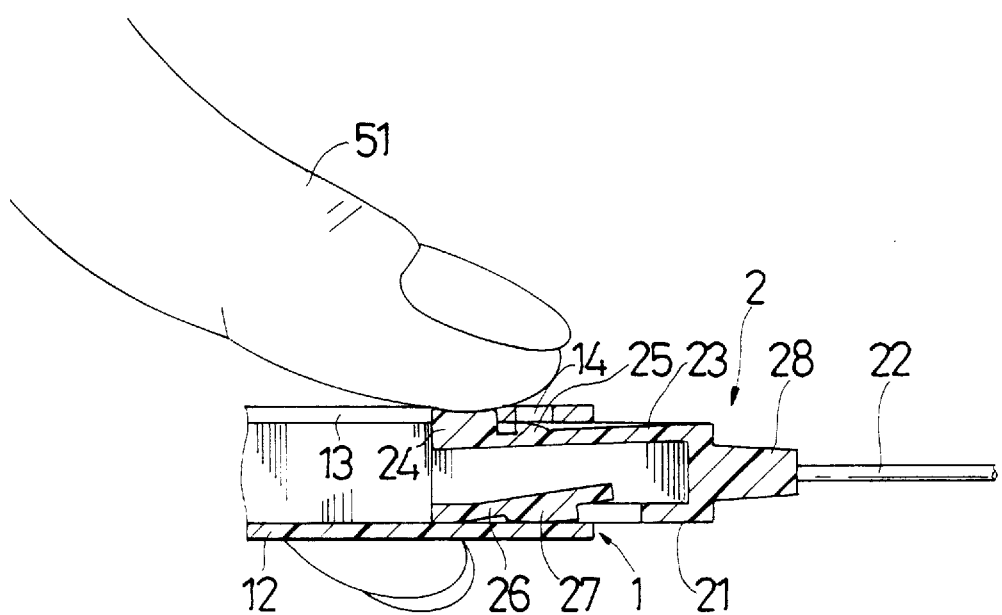
FIG. 5 shows that the depression block is depressed for retracting the metal needle into the housing.
Figure 6:
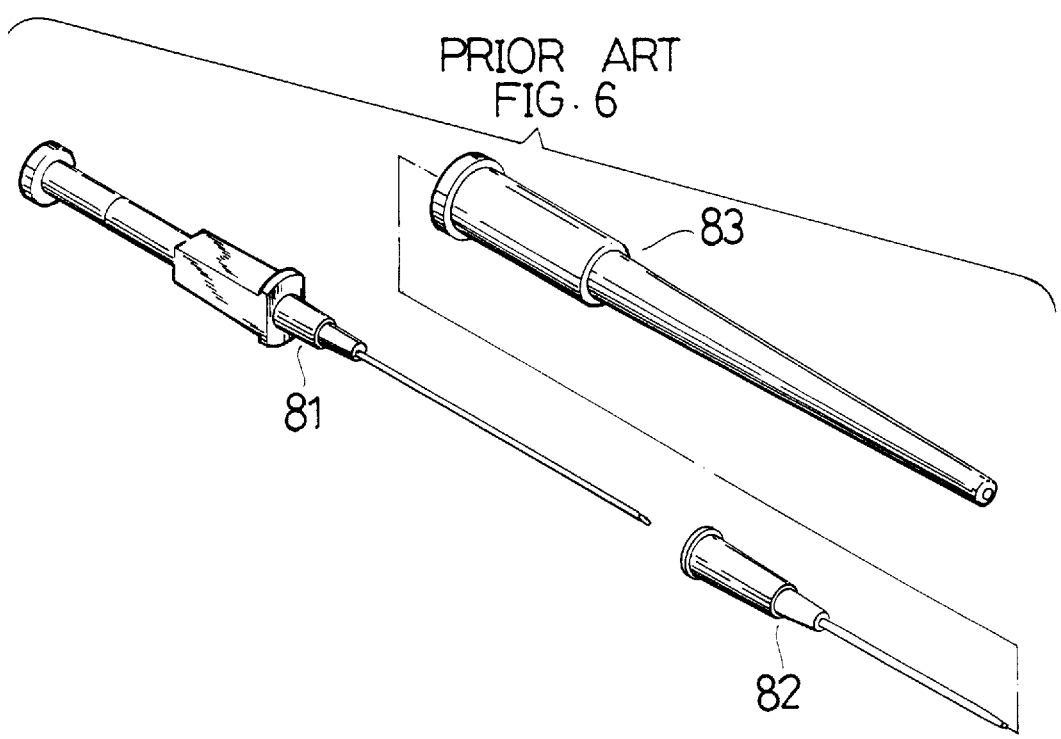
FIG. 6 is a perspective exploded view of a conventional intravenous catheter.

Please refer to FIGS. 3 to 5. In use of the present invention, after the sheath 4 is removed from the metal needle 2, the hard needle 22 together with the soft needle 32 is used to thrust into the skin. After the soft needle 32 gets into the vein, the soft needle 32 is pressed by one hand 5 and then the depression block 24 is pressed down with the thumb 51 of the hand 5 holding the housing 1 so as to downward curve the upper resilient plate 23 and downward move the protuberance 25 into the housing 1. Then the depression block 24 is rearward pushed, whereby the metal needle 2 is entirely retracted into the housing 1 along with depression block 24 and separated from the plastic needle 3. When the lower resilient plate 26 reaches the engaging aperture 15, the projecting block 27 is fitted into the engaging aperture 15 by the resilient restoring force of the lower resilient plate 26. Therefore, the metal needle 2 is prevented from extending out of the housing 1.

In the above operation, the metal needle 2 is retracted into the housing 1 so that the danger of impalement of the hand of the medical personnel is avoided and the safety of the medical personnel is ensured. In addition, the metal needle 2 can be quickly retracted into the housing 1 with one single hand so that the medical personnel has sufficient time for connecting the catheter (not shown) with the plastic needle 3. Therefore, the amount of the blood flowing out will not be too much.

Also, after the metal needle 2 is retracted into the housing 1, the projecting block 27 is not subject to collision or compression so that the metal needle 2 is prevented from extending out of the housing 1. Accordingly, the safety of a transporting worker is ensured.

It is to be understood that the above description and drawings are only used for illustrating one embodiment of the present invention, not intended to limit the scope thereof. Any variation and derivation from the above description and drawings should be included in the scope of the present invention.

What is claimed is:

1. A safety intravenous catheter comprising:

a housing having a semicircular cross-section and a top face and a bottom face, the top face being formed with a slide slot axially extending along the housing and penetrating into an interior of the housing, the housing being formed with a through hole between one end thereof and the slide slot, this end being an open end, while the other end of the housing being a close end, the bottom face being formed with an engaging aperture near the close end of the housing;

a metal needle having a fitting section fitted into the housing, one end of the fitting section being connected with a metal-made hard needle protruding out of the housing, a substantially conic connecting section being connected between the hard needle and the fitting section, a top face of the fitting section having an upper resilient plate one end of which is connected with the fitting section, the upper resilient plate having a depression block slidable within the slide slot and upward projecting from the slide slot, one side of the depression block having a protuberance for fitting into the through hole, a bottom face of the fitting section having a lower resilient plate, one end of the lower resilient plate being connected with the fitting section, the lower resilient plate having a projecting block for fitting into the engaging aperture;

a plastic needle having a needle holder for fitting with the connecting section of the metal needle, one end of the needle holder having a plastic-made soft needle for fitting around the hard needle, the soft needle having a length slightly shorter than that of the hard needle; and a sheath fitting around the metal needle for preventing the hard needle thereof from being exposed.

2. A safety intravenous catheter as claimed in claim 1, wherein the housing has a semicircular cross-section and a plane section is formed on the top face of the housing and an arch section is formed on the bottom face thereof, the fitting section also having a semicircular cross-section.

3. A safety intravenous catheter as claimed in claim 1, wherein the projecting block of the lower resilient plate has a height substantially equal to a depth of the engaging aperture.

* * * * *